(12) United States Patent
Weidner et al.

(10) Patent No.: US 6,235,287 B1
(45) Date of Patent: May 22, 2001

(54) **CERTAIN DITERPENES AND EXTRACTS OR CONCENTRATES OF *CURCUMA AMADA* CONTAINING THEM FOR USE AS MEDICAMENTS**

(75) Inventors: Morten Sloth Weidner, Virum; Morten Just Petersen, Copenhagen; Nina Jacobsen, Frederiksberg, all of (DK)

(73) Assignee: IDA Development A/S, Copenhagen (DK)

(*) Notice: Subject to any disclaimer, the term of this patent is extended or adjusted under 35 U.S.C. 154(b) by 0 days.

(21) Appl. No.: 09/355,858

(22) PCT Filed: Jan. 8, 1999

(86) PCT No.: PCT/DK99/00008
§ 371 Date: Sep. 30, 1999
§ 102(e) Date: Sep. 30, 1999

(87) PCT Pub. No.: WO99/35116
PCT Pub. Date: Jul. 15, 1999

(30) Foreign Application Priority Data

Jan. 9, 1998 (DK) .................................................. 0018/98

(51) Int. Cl.[7] .................................................. A61K 35/78
(52) U.S. Cl. ............................................................. 424/195.1
(58) Field of Search ........................................... 424/195.1

(56) References Cited

U.S. PATENT DOCUMENTS 5,401,777   3/1995   Ammon et al. .
5,709,855 * 1/1998   Bockow .

FOREIGN PATENT DOCUMENTS 2136164    9/1996   (CA) .
29 24 345 A1   1/1981   (DE) .
0 440 885 A1   8/1991   (EP) .
5-85931    4/1993   (JP) .

OTHER PUBLICATIONS

Chang et al., European Journal of Pharmacology, 142:197–205, 1987.
Deodhar et al., Indian J. Med. Res., 71:632–634, 1980.
Goose et al., Immunology, 16:749–760, 1969.
Kumar, Clinical Medicine, Third Edition, Chapter 2, pp. 147–152.
Rao et al. J. Agric. Food Chem., vol. 37, No. 3, pp. 740–743, 1989.*
Zhou et al. Journal of Natural Products, vol. 60, pp. 1287–1293, 1997.*

* cited by examiner

*Primary Examiner*—Francisco Prats
*Assistant Examiner*—Susan D. Coe
(74) *Attorney, Agent, or Firm*—Darby & Darby

(57) ABSTRACT

Certain diterpenes as well as extracts or concentrates of the plant *Curcuma amada* containing at least one such diterpene can be used as medicaments for immunomodulation and for the alleviation of pain. Specifically, they are used for preparing medicaments for the treatment or prevention of hypersensitivity diseases, in particular IgE mediated allergic reactions and conditions as well as autoimmune disorders. Extracts of the plant can i.e. be obtained by extraction or by hydro, steam or vacuum distillation of fresh or dried *Curcuma amada* or parts thereof, preferably the rhizome. Extraction may be performed with water or with a number of different organic solvents, preferably water miscible solvents, or with mixtures thereof. After the primary distillation or extraction process a second step of processing, such as liquid-liquid extraction, column chromatography, steam distillation or vacuum distillation, can be employed to remove or to concentrate and possibly isolate any constituent of the extract.

8 Claims, 1 Drawing Sheet

CERTAIN DITERPENES AND EXTRACTS OR CONCENTRATES OF *CURCUMA AMADA* CONTAINING THEM FOR USE AS MEDICAMENTS

FIELD OF THE INVENTION

The present invention relates to certain diterpenes for use as medicaments and to extracts or concentrates of the plant *Curcuma amada* containing them. Further, the invention relates to pharmaceutical compositions, possibly in the form of dietary supplements or cosmetics, containing at least one of the diterpenes or an extract or concentrate of *Curcuma amada,* as well as to the use of the diterpenes or the extracts or concentrates of *Curcuma amada* for the preparation of medicaments for immunomodulation or the alleviation of pain, and specifically for the suppression of hypersensitivity or inflammatory reactions and the treatment or prevention of diseases associated with hypersensitivity reactions. The invention also relates to a method of preparing an extract of *Curcuma amada.*

BACKGROUND OF THE INVENTION

*Curcuma amada* Roxb. (family Zingiberaceae), also commonly known as Mango Ginger, is cultivated and grows wild throughout India. The herb is rhizomatous with a leafy tuft, 60–90 cm high with white or pale yellow flowers in spikes in the centre of the tuft of leaves.

A number of chemicals have been identified as major components of *Curcuma amada.* Among these are ocimene, dihydro-ocimene, α-pinene, α-curcumene, β-curcumene, linalool, cuminyl alcohol, keto-alcohol, camphor, turmerone, linalyl acetate, safrole, curcumin, myristic acid, car-3-ene, myrcene, 1,8-cineol, limonene, perillene, etc.

Hypersensitivity is defined as a state of altered reactivity in which the body reacts with an exaggerated immune response to a substance (antigen). Hypersensitivity may be caused by exogenous or endogenous antigens.

Hypersensitivity reactions underlie a large number of diseases. Amongst these allergic and autoimmune conditions are of great importance. A classification of hypersensitivity diseases is given by Parveen Kumar and Michael Clark in the textbook Clinical Medicine [1]

Type I hypersensitivity reactions (IgE mediated allergic reactions) are caused by allergens (specific exogenous antigens), e.g. pollen, house dust, animal dandruff, moulds, etc. Allergic diseases in which type I reactions play a significant role include asthma, eczema (atopic dermatitis), urticaria, allergic rhinitis and anaphylaxis.

Type II hypersensitivity reactions are caused by cell surface or tissue bound antibodies (IgG and IgM) and play a significant role in the pathogenesis of myasthenia gravis, Goodpasture's syndrome and Addisonian pernicious anaemia.

Type III hypersensitivity reactions (immune complex) are caused by autoantigens or exogenous antigens, such as certain bacteria, fungi and parasites. Diseases in which type III hypersensitivity reactions play a significant role include lupus erythematosus, rheumatoid arthritis and glomerulonephritis.

Type IV hypersensitivity reactions (delayed) are caused by cell or tissue bound antigens. This type of hypersensitivity plays a significant role in a number of conditions, e.g. graft-versus-host disease, leprosy, contact dermatitis and reactions due to insect bites.

A number of drug classes are available for the treatment of hypersensitivity reactions. Some of these are systemic and some are applied topically.

The corticosteroids are among the most widely used drugs for the treatment of hypersensitivity diseases. Corticosteroids primarily exert their pharmacological action by non-selectively inhibiting the function and proliferation of different classes of immune cells. Hereby hypersensitivity reactions are suppressed. Unfortunately the corticosteroids are associated with a number of serious side effects e.g. immuno-suppression, osteoporosis and skin atrophy (when applied topically).

SUMMARY OF THE INVENTION

We have found that compounds of formula I:

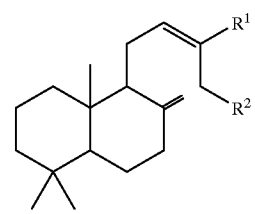

wherein $R^1$ and $R^2$ are independently $CH_2OH$ or $CHO$, and extracts or concentrates of *Curcuma amada* containing at least one compound of formula I significantly suppress hypersensitivity reactions.

Compared to the corticosteroids the compounds of formula I or extracts of *Curcuma amada* containing compounds according to formula I have the advantage of not being associated with any serious side effects.

Due to their pharmacological effects compounds of formula I or extracts of *Curcuma amada* containing compounds according to formula I can be employed for the following therapeutic applications:

Immunomodulation.

Treatment or prevention of hypersensitivity diseases.

Treatment or prevention of IgE mediated allergic reactions and conditions.

Treatment or prevention of autoimmune disorders.

Alleviation of pain.

Accordingly the present invention provides a pharmaceutical composition, dietary supplement or cosmetic containing at least one compound of formula I or an extract or concentrate of *Curcuma amada* and a pharmaceutically acceptable carrier.

A "dietary supplement" is defined, according to the U.S. Food and Drug Administration in the Dietary Supplement Health and Education Act of 1994 (DSHEA).

The DSHEA gives the following formal definition of a "dietary supplement":

A dietary supplement:

is a product (other than tobacco) that is intended to supplement the diet that bears or contains one or more of the following dietary ingredients: a vitamin, a mineral, an herb or other botanical, an amino acid, a dietary substance for use by man to supplement the diet by increasing the total daily intake, or a concentrate, metabolite, constituent, extract, or combinations of these things.

is intended for ingestion in pill, capsule, tablet, or liquid form.

Similar definitions exist in other parts of the world, e.g. in Europe. Different denominations concerning "dietary supplements" or similar food products are used around the world, such as "food supplements", "neutra-ceuticals", "functional foods" or simply "foods". In the present context the term "food supplement" covers any such denomination or definition.

More specifically the present invention provides the use of at least one compound of formula I or an extract or concentrate of *Curcuma amada* for preparing a medicament for immunomodulation, for the suppression of hypersensitivity reactions such as IgE mediated allergic reactions and autoimmune reactions, and for the alleviation of pain.

Thus, according to the invention at least one compound of formula I or an extract or concentrate of *Curcuma amada* can be used in a method for the treatment or prevention of a hypersensitivity disease in an individual, which comprises administering such substances or a pharmaceutical composition or dietary supplement containing it to said individual; and the invention comprises the use of at least one compound of formula I or an extract or concentrate of *Curcuma amada* for preparing a medicament for the treatment or prevention of hypersensitivity diseases.

Also, according to the invention at least one compound of formula I or an extract or concentrate of *Curcuma amada* can be used in a method for the treatment or prevention of an autoimmune disorder in an individual, which comprises administering such substances or a pharmaceutical composition or dietary supplement containing it to said individual; and the invention comprises the use of at least one compound of formula I or an extract or concentrate of *Curcuma amada* for preparing a medicament for the treatment or prevention of autoimmune disorders.

Further, according to the invention at least one compound of formula I or an extract or concentrate of *Curcuma amada* can be used in a method for the treatment or prevention of an IgE mediated allergic reaction or condition in an individual, which comprises administering such substances or a pharmaceutical composition or dietary supplement containing them to said individual; and the invention comprises the use of at least one compound of formula I or an extract or concentrate of *Curcuma amada* for preparing a medicament for the treatment or prevention of IgE mediated allergic reactions and conditions.

Also, according to the invention at least one compound of formula I or an extract or concentrate of *Curcuma amada* can be used in a method for the alleviation of pain in an individual, which comprises administering such substances or a pharmaceutical composition or dietary supplement containing them to said individual; and the invention comprises the use of at least one compound of formula I or an extract or concentrate of *Curcuma amada* for preparing a medicament or dietary supplement for the alleviation of pain.

Further, the invention provides a method of preparing an extract of *Curcuma amada*, which comprises extracting said plant or parts thereof, preferably the rhizome, with an extraction agent comprising an organic solvent or water or mixtures thereof and subsequently, if necessary, removing the extraction agent to obtain an extract suitable for utilisation.

DETAILED DESCRIPTION OF THE INVENTION

Figure 1:
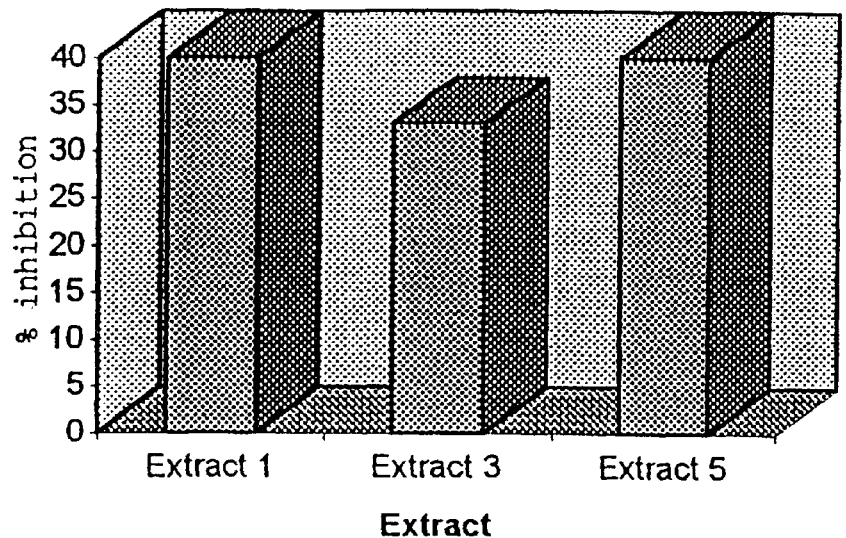
FIG. 1 shows the percent inhibition of allergic activity compared to the control for the groups treated with the test extracts in the assay using p.o. administration.

Surprisingly it has been found that compounds of formula I or extracts or concentrates of *Curcuma amada* containing at least one compound of formula I exert pharmacological actions relevant to the therapeutic treatment of conditions associated with hypersensitivity reactions and pain.

A particularly important compound according to formula I is Labda-8(17),12-diene-15,17-dial, which is shown in formula II:

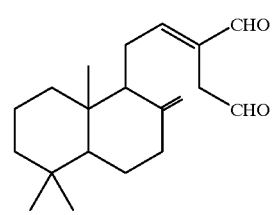

II

In all embodiments of the invention Labda-8(17),12-diene-15,17-dial is preferred among the compounds according to formula I.

More specifically compounds of formula I or extracts or concentrates of *Curcuma amada* provide the following pharmacological effects upon administration to the living organism:

Immunomodulation.

Suppression of hypersensitivity reactions.

Suppression of IgE mediated allergic reactions.

Suppression of autoimmune reactions.

Reduction of pain.

These actions provide part of the rationale for the following therapeutic applications of *Curcuma amada* or parts thereof or extracts or components thereof:

A method for the treatment or prevention of hypersensitivity diseases characterised by the administration of at least one compound of formula I or an extract or concentrate of *Curcuma amada*. The therapeutic action may be relevant to all known diseases associated with hypersensitivity reactions. Below autoimmune disorders and IgE mediated allergic conditions are described more in detail. Besides these specific therapeutic areas the action of at least one compound of formula I or an extract or concentrate of *Curcuma amada* is relevant to all known conditions and diseases associated with hypersensitivity reactions and the following examples are not limiting with respect to this: infections (viral, bacterial, fungal, parasitic, etc.), cold and flu, contact dermatitis, insect bites, allergic vasculitis, postoperative reactions, transplantation rejection (graft-versus-host disease), etc.

A method for the treatment or prevention of autoimmune disorders characterised by the administration of at least one compound of formula I or an extract or concentrate of *Curcuma amada*. The applicant puts forward the hypothesis that the therapeutic action is due to the immunomodulating and suppressing effect on hypersensitivity reactions of compounds of formula I or extracts or concentrates of *Curcuma amada*. The therapeutic action may be relevant to all known autoimmune disorders and the following examples are not limiting with respect to this: Autoimmune hepatitis, primary biliary cirrhosis, primary sclerosing cholangitis, autoimmune hemolytic anemias, Grave's disease, myasthenia gravis, Type 1 diabetes mellitus, inflamatory myopathies, multiple sclerosis, Hashimoto's thyreoiditis, autoimmune adrenalitis, Crohn's disease, ulcerative colitis, glomerulonephritis, progressive systemic sclerosis (scleroderma), Sjögren's disease, lupus erythematosus, primary vasculitis, rheumatoid arthritis, juvenile arthritis, mixed connective tissue disease, psoriasis, pemfigus, pemfigoid, dermatitis herpetiformis, etc.

A method for the treatment or prevention of IgE mediated allergic reactions and conditions characterised by the administration of at least one compound of formula I or an extract or concentrate of *Curcuma amada*. The applicant puts forward the hypothesis that the therapeutic action is due to the suppressing effect on hypersensitivity reactions of compounds of formula I or extracts or concentrates of *Curcuma amada*. The therapeutic action may be relevant to all known IgE mediated allergic reactions and conditions and the following examples are not limiting with respect to this: asthma, eczema (e.g. atopic dermatitis), urticaria, allergic rhinitis, anaphylaxis, etc.

A method for the treatment or prevention of any condition associated with pain characterised by the administration of at least one compound of formula I or an extract or concentrate of *Curcuma amada*. The applicant puts forward the hypothesis that the therapeutic action is related to immunomodulation, possibly to suppressing effects on hypersensitivity reactions.

A preferred embodiment of the invention is an extract of *Curcuma amada*. Extracts according to the invention can i.a. be obtained by extraction or distillation (e.g. hydro, steam or vacuum distillation) of fresh or dried *Curcuma amada* or parts thereof, preferably the rhizome. Extraction may be performed with a number of different organic solvents, preferably water miscible solvents, and mixtures thereof with water. The extraction can also be performed with water immiscible solvents, such as alkanes. The extraction can be performed hot or cold by the employment of any extraction technology e.g. maceration, percolation or supercritical extraction.

The preferred extraction solvents are pentane, hexane, heptane, acetone, methyl ethyl ketone, ethyl acetate, lower alkanols having 1 to 4 carbon atoms and mixtures thereof with water. The preferred extraction temperature is close to the boiling point of the employed solvent due to extraction efficacy, but lower temperatures are also applicable making necessary a longer period of extraction.

Supercritical extraction (e.g. performed with $CO_2$) is also a preferred mode of extraction.

By changing the composition of the applied solvent the extraction can be made more selective for certain constituents of *Curcuma amada* thus enhancing or reducing their content in the finished extract. For example the content of phenolic glycosides can be increased by employing a more hydrophilic solvent while the content of sesquiterpenes in the finished product can be enhanced by employing a more lipophilic solvent.

After the primary extraction process a second step of processing, such as liquid-liquid extraction, column chromatography or any type of distillation, can be employed to remove or to concentrate and possibly isolate any constituent of the extract. Hereby any constituent of *Curcuma amada* can be avoided or concentrated in the finished extract, e.g. ocimene, dihydro-ocimene, α-pinene, α-curcumene, β-curcumene, linalool, cuminyl alcohol, keto-alcohol, camphor, turmerone, linalyl acetate, safrole, curcumin, myristic acid, car-3-ene, myrcene, 1,8-cineol, limonene or perillene. Thus the content of any component of *Curcuma amada* can be standardised in the finished extract for the purpose of manufacturing a pharmaceutical composition.

According to the invention, compounds of formula I may be extracted from other plants than *Curcuma amada,* such as the seeds of *Alpinia galanga* (L.).

According to the invention at least one compound of formula I or an extract or concentrate of *Curcuma amada* can be combined with any other active ingredient or plant extract to potentiate the therapeutic action. Consequently, we propose to combine *Curcuma amada* or parts thereof or extracts or components thereof with eicosapentaenoic acid from fish oils or γ-linolenic acid for any of the above mentioned therapeutic applications of *Curcuma amada* or parts thereof or extracts or components thereof.

Furthermore it is obvious that in the use according to the invention for preparing medicaments at least one compound of formula I or an extract or concentrate of *Curcuma amada* may be mixed with additives such as surfactants, solvents, thickeners, stabilisers, preservatives, antioxidants, flavour etc. to obtain a desirable product formulation. Similarly, the pharmaceutical compositions, dietary supplements or cosmetics according to the invention may further contain such additives. There are no limitations to the route of administration or dosage form of the formulation and the following examples are not limiting with respect to this: tablets, capsules, fluids, granulates, gels, ointments, liniments, emulsions (e.g. cremes and lotions), sprays (e.g. aerosol), eye drops, etc. Optionally, the composition may also contain surfactants such as bile salts, polyoxyethylene-sorbitan-fatty acid esters or polyalcohol mixed chain-length fatty acid esters for improving dispersibility of the composition in the digestive fluids leading to improved bioavailability or for obtaining the final dosage form of the composition.

EXAMPLES

Example 1

An extract of *Curcuma amada* according to the invention was prepared as follows:

50 g dried root of *Curcuma amada* was extracted with 500 ml of boiling methanol for 3 hours. This extraction was repeated with the same starting material using again 500 ml methanol in 3 hours. Thereafter the extract was filtrated and evaporated to dryness under vacuum. Thus, 2.5 g of an amber-coloured liquid extract was obtained suitable for the manufacture of tablets, hard gelatine capsules, ointment, nasal drops, etc.

Example 2

An extract of *Curcuma amada* according to the invention was prepared as follows:

50 g dried root of *Curcuma amada* was extracted with 500 ml of boiling 50% methanol for 3 hours. This extraction was repeated with the same starting material using again 500 ml ethanol in 3 hours. Thereafter the extract was filtrated and evaporated to dryness under vacuum. Thus, 2.8 g of an amber-coloured liquid extract was obtained suitable for the manufacture of tablets, hard gelatine capsules, ointment, nasal drops, etc.

Example 3

An extract of *Curcuma amada* according to the invention was prepared as follows:

50 g dried root of *Curcuma amada* was extracted with 500 ml of boiling acetone for 3 hours. This extraction was repeated with the same starting material using again 500 ml acetone in 3 hours. Thereafter the extract was filtrated and evaporated to dryness under vacuum. Thus, 2.1 g of an amber-coloured liquid extract was obtained suitable for the manufacture of tablets, hard gelatine capsules, ointment, nasal drops, etc.

Example 4

An extract of *Curcuma amada* according to the invention was prepared as follows:

50 g dried root of *Curcuma amada* was extracted with 500 ml of boiling ethyl acetate for 3 hours. This extraction was repeated with the same starting material using again 500 ml ethyl acetate in 3 hours. Thereafter the extract was filtrated and evaporated to dryness under vacuum. Thus, 1.4 g of an amber-coloured liquid extract was obtained suitable for the manufacture of tablets, hard gelatine capsules, ointment, nasal drops, etc.

Example 5

An extract of *Curcuma amada* according to the invention was prepared as follows:

50 g dried root of *Curcuma amada* was extracted with 500 ml of boiling hexane for 3 hours. This extraction was repeated with the same starting material using again 500 ml hexane in 3 hours. Thereafter the extract was filtrated and evaporated to dryness under vacuum. Thus, 1.8 g of an amber-coloured liquid extract was obtained suitable for the manufacture of tablets, hard gelatine capsules, ointment, nasal drops, etc.

Example 6

An extract of *Curcuma amada* according to the invention was prepared as follows:

Dried root of *Curcuma amada* was steam-distilled. A golden-coloured liquid extract was obtained suitable for the manufacture of hard gelatine capsules, ointment, na- sal drops, etc.

Example 7

An extract of *Curcuma amada* according to the invention was formulated in a preparation for use as nasal drops or nasal spray, according to the following prescription:

For the preparation of 100 g nasal spray, 1 mg/ml:

| a) Extract of Curcuma amada: | 0.05 g |
| b) Cremophor RH 40, BASF: | 2.00 g |
| c) Ethylenediamine tetraacetic acid, Fluka: | 0.05 g |
| d) Benzalkoniumchloride, Sigma: | 0.01 g |
| e) Sodium chloride, Merck: | 0.89 g |
| f) Milli-Q water, Millipore: | 97.00 g |

Procedure a) is dispersed in b) while heated to 37° C. on a water bath; c), d) and e) are added. After mixing, f) is added little by little under vigorous mixing.

A nasal spray formulation prepared according to the above prescription using an extract of *Curcuma amada* prepared as described in example 5, was tested by 5 volunteers. The nasal spray was reported to be effective against allergic rhinitis.

Example 8

An extract of *Curcuma amada* according to the invention was formulated in an ointment preparation according to the following prescription:

For the preparation of 30 g ointment, 0,5%:

| a) Extract of Curcuma amada: | 0.3 g |
| b) Cremeol E-45, Århus Oliefabrik A/S: | 19.5 g |
| c) Volatile Silicone VS72, Bionord A/S: | 9.0 g |
| d) Cremeol HF-52 SPC, Århus Oliefabrik A/S: | 1.2 g |

Procedure d) is melted at approx. 100° C.; and b) is added under continuous heating and mixing. Then c) is added, and the mixture is cooled to room temperature. Finally a) is added, and the formulation is mixed. The formulation is filled on tubes, ointment jars or similar.

Ointment formulations prepared according to the above prescription using extracts of *Curcuma amada* prepared as described in Example 1 and Example 3, respectively, were tested by 5 volunteers. Both ointment preparations were reported to be effective against atopic eczema, by alleviating eczema rash and itching.

Example 9

Study Object

Four extracts of *Curcuma amada* according to the invention were prepared as described in examples 1, 3, 4 and 5, hereafter correspondingly called Extract 1, 3, 4 and 5, respectively, were investigated in this study.

Summary of the Study

Background

The objective of the study was to evaluate the antiallergic effect of the four extracts of *Curcuma amada* in a well established assay for anti-allergic activity, the Passive Cutaneous Anaphylaxis (PCA) test.

Methods

The assay was performed according to Goose and Blair[2].

Test substances (Extract 1, 3, and 5 ; 500 mg/kg), and vehicle (control) were given by oral administration(p.o.) to a group of 3 Long Evans derived rats, passively sensitized 16 hours earlier by intradermal injection of reaginic (IgE) antiovalbumin serum (0.05 ml). Within 30 minutes after administration of test substance, the animals were challanged i.v. with a mixture of ovalbumin (1 mg) and Evans Blue dye (5 mg) and sacrificed 30 minutes later. Inhibition of the resulting PCA blue colored wheal indicates possible antiallergic activity.

Furthermore, a similar PCA test using i.v. administration of the test substances (Extract 1, 3, 4 and 5) and vehicle (control) was performed. The test substances were administered i.v. (20 mg/kg) to a group of 3 Long Evans derived rats passively sensitized 16 hours earlier by intradermal injection of reagenic (IgE) antiovalbumin serum (0.05 ml). Immediately after administration of test substance, the animals were challanged i.v. with a mixture of ovalbumin (1 mg) and Evans Blue dye (5 mg) and sacrificed 30 minutes later.

Findings

Figure 2:
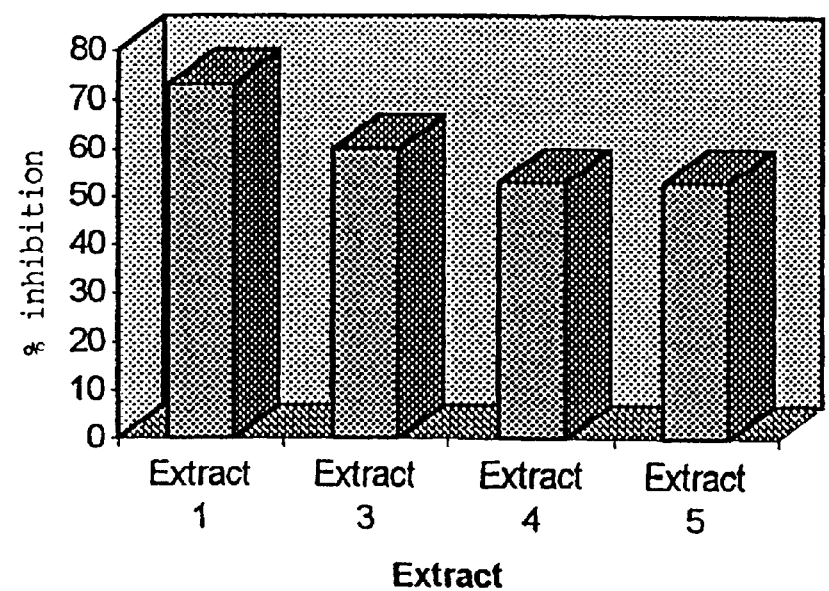
FIG. 2 shows the percent inhibition of allergic activity compared to the control for the groups treated with the test extracts in the assay using i.v. administration. The anti-allergic activity was determined using the Passive Cutaneous Anaphylaxis assay.

The percent inhibition (mean) compared to the vehicle (control) of the PCA blue colored wheal for the groups treated with the test extracts in the assay using p.o. administration is shown in FIG. 1. The similar results obtained in the assay using i.v. administration is shown in FIG. 2.

In the assay using p.o. administration, all three extracts (Extract 1, 3 and 5) revealed a marked % inhibition, as shown in FIG. 1, compared to the vehicle (control). As shown in FIG. 2, the results from the assay using i.v. administration revealed even higher % inhibition compared to the vehicle (control).

Interpretation

In this study it is clearly demonstrated that extracts from *Curcuma amada* according to the invention and prepared as described in example 1, 3, 4 and 5, possess powerful anti-allergic activities.

Example 10

Study Object

An extract of *Curcuma amada,* according to the invention, was compared with placebo in a well established model of inflammation in the skin.

Summary of the Study

Background

The objective of the study was to test an extract according to the invention in a well established model of eczema, arachidonic acid induced inflammation in the mouse.

Methods

The assay was performed according to Chang et al[3]. Ear inflammation was induced by topical application of arachidonic acid (5 mg in 20 μl acetone). Groups of five BALB/c mice were pre-treated 30 minutes before arachidonic acid application and 15 minutes after (post-treatment) with the extract of *Curcuma amada* prepared in example 3 (1,5 mg per ear per challenge).

The degree of swelling was recorded four hours after arachidonic acid application.

Findings

The mean percent inhibition of ear swelling was 32% as compared to the control. The extract demonstrated a statistically significant effect as compared to the control (p<0,05, Wilcoxon rank sum test).

Interpretation

The study clearly shows that the extract according to the invention possesses marked anti-inflammatory effects.

REFERENCES

1. Kumar, P. and Clark, M.: "Clinical Medicine", 3rd edition, Baillière Tindall, London 1994, pp. 147–150.
2. Goose, J. and Blair, A. M.: Immunol. 16: 749, 1969.
3. Chang, J. et al.: Eur. J. Pharmacol. 142: 197, 1987.

What is claimed is:

1. A composition comprising an extract of *Curcuma amada* which comprises at least one compound of formula I

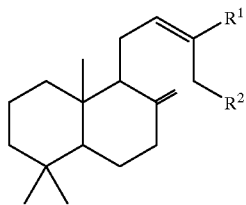

(I)

wherein $R^1$ and $R^2$ are independently $CH_2OH$ or CHO and which further comprises at least one compound selected from the group consisting of ocimene, dihydro-ocimene, α-pinene, α-curcumene, β-curcumene, linalool, cuminyl alcohol, keto-alcohol, turmerone, linalyl acetate, safrole, car-3-ene, myrcene, 1-8-cineol, limonene and perillene.

2. A composition according to claim 1, which further comprises γ-linolenic acid or eicosapentaenoic acid.

3. A composition according to claim 1, which is in the form of a dietary supplement.

4. A composition according to claim 1, which is in the form of a topical preparation.

5. A method for the treatment or amelioration of a hypersensitivity disease in an individual, which comprises administering to said individual an effective amount of a member selected from the group consisting of: (a) at least one compound of formula I

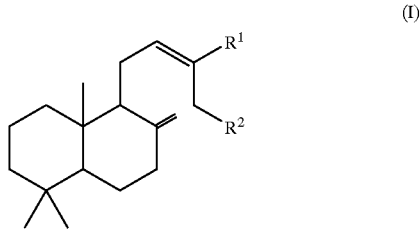

(I)

wherein $R^1$ and $R^2$ are independently $CH_2OH$ or CHO (b) an extract or concentrate of *Curcuma amada* which comprises at least one compound of formula I; and (c) an extract or concentrate of *Curcuma amada* which comprises at least one compound of formula I and at least one compound selected from the group consisting of ocimene, dihydro-ocimene, α-pinene, α-curcumene, β-curcumene, linalool, cuminyl alcohol, keto-alcohol, turmerone, linalyl acetate, safrole, car-3-ene, myrcene, 1,8-cineol, limonene and perillene to treat or ameliorate said hypersensitivity disease.

6. A method for the treatment or amelioration of an autoimmune disease or an inflammatory disease in an individual, which comprises administering to said individual an effective amount of a member selected from the group consisting of: (a) at least one compound of formula I

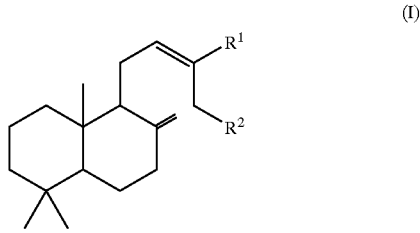

(I)

wherein $R^1$ and $R^2$ are independently $CH_2OH$ or CHO (b) an extract or concentrate of *Curcuma amada* which comprises at least one compound of formula I; and (c) an extract or concentrate of *Curcuma amada* which comprises at least one compound of formula I and at least one compound selected from the group consisting of ocimene, dihydro-ocimene, α-pinene, α-curcumene, β-curcumene, linalool, cuminyl alcohol, keto-alcohol, turmerone, linalyl acetate, safrole, car-3-ene, myrcene, 1,8-cineol, limonene and perillene to treat or ameliorate said autoimmune or inflammatory disease.

7. A method for the treatment or amelioration of an IgE mediated allergic reaction or condition in an individual, which comprises administering to said individual an effective amount of a member selected from the group consisting of: (a) at least one compound of formula I

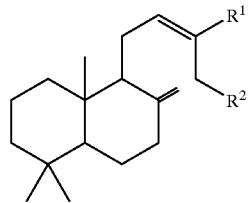

(I)

wherein $R^1$ and $R^2$ are independently $CH_2OH$ or CHO (b) an extract or concentrate of *Curcuma amada* which comprises at least one compound of formula I; and (c) an extract or concentrate of *Curcuma amada* which comprises at least one compound of formula I and at least one compound selected from the group consisting of ocimene, dihydro-ocimene, α-pinene, α-curcumene, β-curcumene, linalool, cuminyl alcohol, keto-alcohol, turmerone, linalyl acetate, safrole, car-3-ene, myrcene, 1,8-cineol, limonene and perillene to treat or ameliorate said IgE mediated allergic reaction or condition.

8. A method for the alleviation of pain in an individual in need thereof, which comprises administering an effective amount of the composition of claim 1 to said individual in need thereof.

* * * * *